United States Patent [19]
Francis et al.

[11] Patent Number: 5,752,965
[45] Date of Patent: May 19, 1998

[54] APPARATUS AND METHOD FOR PRODUCING A REINFORCED SURGICAL FASTENER SUTURE LINE

[75] Inventors: Ralph T. Francis, St. Anthony; Mark E. Hughes, Circle Pines; Anne E. Claeson, Minneapolis, all of Minn.; Joel Cooper, St. Louis, Mo.

[73] Assignee: Bio-Vascular, Inc., St. Paul, Minn.

[21] Appl. No.: 734,113

[22] Filed: Oct. 21, 1996

[51] Int. Cl.$^6$ ............................................. A61B 17/00
[52] U.S. Cl. ...................... 606/151; 227/178.1; 227/180.1
[58] Field of Search ................................. 606/148, 151, 606/156; 623/2, 11; 600/36, 37; 602/48, 50

[56] References Cited

U.S. PATENT DOCUMENTS

| | | | |
|---|---|---|---|
| 4,354,628 | 10/1982 | Green | 227/19 |
| 4,508,253 | 4/1985 | Green | 227/19 |
| 4,520,817 | 6/1985 | Green | 128/305 |
| 4,568,009 | 2/1986 | Green | 227/19 |
| 4,681,588 | 7/1987 | Ketharanathan | 623/11 |
| 4,728,020 | 3/1988 | Green et al. | 227/19 |
| 4,930,674 | 6/1990 | Barak | 227/179 |
| 4,932,960 | 6/1990 | Green et al. | 606/220 |
| 5,141,144 | 8/1992 | Foslien et al. | 227/176 |
| 5,156,614 | 10/1992 | Green et al. | 606/220 |
| 5,263,629 | 11/1993 | Trumbull et al. | 227/181 |
| 5,397,324 | 3/1995 | Carroll et al. | 606/139 |
| 5,441,193 | 8/1995 | Gravener | 227/176 |
| 5,503,638 | 4/1996 | Cooper et al. | 623/11 |
| 5,542,594 | 8/1996 | McKean et al. | 227/178.1 |

OTHER PUBLICATIONS

"Clinical Applications of Bioabsorbable PGA Sheets for Suture Reinforcement and Use as Artificial Pleura", Tatsuo Nakamura, Yasuhiko Shimizu, Hiroshi Mizuno, Shigeki Hitomi, Morihisa Kitano, and Seiichi Matsunobe; Japan Lung Surgery Journal 40: 10. 8(1826) 1992.

"Reinforced Staple Line in Severely Emphysematous Lungs", F.-M. Juettner, MD, P. Kohek, MD, H. Pinter, MD, G. Klepp, MD and G. Friehs, MD, Graz, Austria, Journal of Thorac and Cardiovasc Surgery 1989;97:362-3.

"Median Sternotomy for Bilateral Resection of Emphysematous Bullae", Oriane Lima, MD, Luis Ramos, MD, Paulo Di Biasi, MD, Luis Judice, MD, Niteroi and Rio de Janeiro, Brazil, and Joel D. Cooper, MD, Toronto, Ontario, Canada, Journal of Thorac and Cardiovasc Surgery 82:892-897, 1981.

"The Current Status of Surgery for Bullous Emphysema", John E. Connolly, MD, and Archie Wilson, MD (by invitation), Irvine, California, Journal of Thorac and Cardiovasc Surgery 1989;97:351-61.

*Primary Examiner*—Gary Jackson
*Attorney, Agent, or Firm*—Haugen and Nikolai, P.A.

[57] ABSTRACT

An apparatus and method for providing reinforced surgical fastener suture lines to prevent tissue tearing and fluid leakage following the creation of an anastomosis, the closing of margins following the removal of diseased tissue, and/or the ligating and dividing of individual blood vessels. A retainer assembly is provided having an alignment frame and a pressure equalization member. The alignment frame includes an internally disposed receiving area for housing the pressure equalization member and a pair of guide channels disposed in fluid communication with the receiving area for guiding the jaw members of a surgical fastener applying device into contact with pledget material disposed within the receiving area. Any number of surgical fastener applying devices may be retrofitted to provide reinforced surgical fastener suture lines by applying an adhesive along the length of the pledget material, positioning the jaw members of a surgical fastener applying device within the guide channels, and closing the surgical fastener applying device such that the jaw members are brought into compressed contact with the adhesive-laden pledget material. The surgical fastener applying device may then be opened with the pledget material releasibly attached to the jaw members, the jaw members positioned about a section of body tissue, and the surgical fastener applying device fired to create a reinforced suture line boasting reduced tissue tearing and reduced fluid leakage.

21 Claims, 7 Drawing Sheets

APPARATUS AND METHOD FOR PRODUCING A REINFORCED SURGICAL FASTENER SUTURE LINE

BACKGROUND OF THE INVENTION

I. Field of the Invention

The present invention relates generally to instruments for applying surgical fasteners, such as staples, clips, and the like, for the purposes of creating an anastomosis, closing the margins following the removal of diseased tissue, and/or ligating and dividing individual blood vessels. More particularly, the present invention relates to an apparatus and method for positioning an article of pledget material onto a surgical fastener applying device for the purposes of creating a reinforced surgical fastener suture line to prevent subsequent tearing of the tissue, the escape of bodily fluids from the surgical site, and the entry of foreign materials into the surgical site.

II. Discussion of the Prior Art

Through time, surgical fastener applying devices have enjoyed widespread popularity due to the ease of use, improved perfusion characteristics, and enhanced healing offered above traditional manual suturing techniques. In general, such surgical fastener applying devices include a pair of cooperating jaw members having apposed working surfaces which are capable of selectively converging upon and compressing a length of body tissue such that, when fired, the device will force one or more surgical fasteners through the subject body tissue to form a surgical fastener suture line. As used herein, the term "surgical fastener suture line" is not meant to imply the use of thread, cat gut, or the like, but instead is intended to identify the joining of two surfaces or edges of body tissue together along a line through the use of surgical fasteners such as staples, clips, and the like. To accomplish the formation of a surgical fastener suture line, one jaw member is equipped with a fastener cartridge having at least two laterally spaced rows of surgical fasteners, while the other jaw member is furnished with an anvil having fastener-closing depressions and/or interlocking retaining elements aligned with the rows of surgical fasteners in the cartridge. An exemplary use of surgical fastener applying devices is found in lung reduction surgery, wherein the surgical fastener applying device is used to place a plurality of staggered rows of closely spaced surgical fasteners through a section of lung tissue at the margin between healthy and diseased tissue. The diseased portion of the lung may then be excised by trimming along the outermost row of surgical fasteners or by dividing the tissue between the various rows of surgical fasteners.

The prior art surgical fastener applying devices employ a variety of different opening and closing mechanisms through which the fastener cartridge and the anvil cartridge may be brought into position about the subject body tissue. For example, U.S. Pat. No. 4,354,628 to Green and U.S. Pat. No. 5,141,144 to Foslien et al. disclose surgical fastener applying devices with pivotally related jaw members that extend between an open condition, wherein the jaw members diverge from one another about a connecting pin to accept the subject body tissue therebetween, and a closed condition, wherein the jaw members are positioned generally parallel to one another in a compressed relationship over the subject body tissue. Another popular opening and closing mechanism is disclosed in U.S. Pat. No. 4,568,009 to Green and U.S. Pat. No. 4,508,253 to Green, wherein the individual jaw members are maintained generally parallel to one another at all times and provided with an actuator for linearly translating the jaw members towards and away from one another to respectively close and open the surgical fastener applying device. Surgical fastener applying devices may be designed to apply the surgical fasteners in sequence, to thereby progressively form the surgical fastener suture line, or to apply all the surgical fasteners simultaneously, to thereby form the surgical fastener suture line with a single firing of the surgical fastener applying device.

The prior art surgical fastener applying devices may also employ a host of different surgical fasteners that range widely in both design and composition. For example, surgical fasteners may take the form of a conventional staple and/or a two-piece interlocking fastener and may be constructed from metal and/or non-metallic resinous material. U.S. Pat. No. 4,520,817 to Green discloses the use of conventional staples, wherein the staple legs are driven through the tissue and cinched by depressions formed in the anvil to bend the legs and thereby secure the staples in the tissue. A two-piece surgical fastener is disclosed in U.S. Pat. No. 5,156,614 to Green et al., comprising a fastener member disposed in the cartridge and a retainer member disposed in the anvil, wherein the legs of the fastener member are driven through the tissue and made to interlock with the retainer member to secure the fasteners in the subject body tissue. While surgical fasteners are typically constructed from biologically inert metal which remain permanently in the body, biologically absorbable metal surgical fasteners are also known and contemplated. In similar fashion, surgical fasteners constructed from non-metallic resinous materials may be either biologically absorbable or inert and permanent.

While the use of surgical fastener applying devices provides an improvement over traditional manual suturing, a common drawback exists in that a certain amount of tissue tearing and fluid leakage may be experienced along the surgical fastener suture line following the particular procedure. Tissue tearing may be particularly prevalent and troublesome when dealing with diseased and/or body tissue which is otherwise weakened and incapable of withstanding the ordinary pressures and stresses associated with surgical fastener suture lines. Fluid leakage typically stems from areas along the surgical fastener suture line where the body tissue is either inadequately compressed, having a lack of contact area between the subject body tissue, or due to the distension of the body tissue at the points where the surgical fasteners penetrate therethrough. In this regard, various efforts have been undertaken to fortify surgical fastener suture lines to minimize the degree to which the surgical fasteners tear out of the body tissue and the degree to which fluid is permitted to leak therethrough.

One attempt at combating such fluid leakage and tearing entails modifying the design and pattern of the surgical staples to increase the contact area between the compressed portions of body tissue. While this technique is effective in bolstering the strength of surgical fastener suture lines, a significant drawback exists in that it requires the use of custom-made surgical fasteners and/or custom-made surgical fastener applying devices, thus making this technique costly to implement. A further drawback exists in that, by increasing the size and/or number of rows of surgical fasteners, the size of the surgical fastener applying device must also be increased which limits the utility of the instrument. This is a especially troublesome when engaging in minimally invasive or laparoscopic surgery since access to the operative region requires the head of the surgical fastener applying device to pass through trocars of very small diameter. Another potential drawback exists in that increasing the number of surgical fasteners within a given area makes the task of aligning the surgical fasteners in the cartridge with the fastener-closing depressions and/or interlocking retaining elements in the anvil increasingly burdensome and problematic.

Other efforts at combating fluid leakage and tissue tearing along surgical fastener suture lines have focused on positioning an article of pledget material between the surgical fasteners and the subject body tissue. This technique is advantageous for several reasons. First, it serves to more uniformly distribute pressure along the surgical fastener suture line to increase the contact area between the compressed portions of body tissue, thereby reducing the propensity for fluid leakage along the surgical fastener suture line. Second, it results in a decreased incidence of tissue tearing by adding structural support between the subject tissue and the surgical fasteners, thus increasing the overall structural integrity of the surgical fastener suture line. Third, the pledget material may be selected to absorb any fluid that does leak through the surgical fastener suture line. Lastly, this technique accomplishes the goals of reducing fluid leakage and tearing without modifying the pattern or design of the surgical fasteners, thereby avoiding any further difficulties in aligning the surgical fasteners in the cartridge with the fastener-closing depressions and/or retaining elements in the anvil.

U.S. Pat. No. 5,263,629 to Trumbull et al. represents one such effort, wherein disposable anvil and fastener cartridges are provided having pledget material disposed thereon for producing a reinforced surgical fastener suture line. However, while the device and method of the '629 patent is effective in providing a fortified suture line, a substantial drawback exists in that the improvement is restricted to the use of only those surgical fastener applying devices which employ disposable cartridges and anvils. Such a restriction to disposable anvils and cartridges is disadvantageous in that it effectively limits the ability to retrofit other types of surgical fastener applying devices, such as those having permanent or non-disposable anvil and cartridge portions, thereby limiting the scope and versatility of the invention. Moreover, these disposable anvils and fastener cartridges must be custom made to accommodate the pledget material which, it will be appreciated, increases the costs associated with utilizing this particular device, both in terms of materials, tooling, and labor for manufacturing the custom anvil and cartridge portions, as well as positioning and securing the pledget material on the anvils and cartridges.

U.S. Pat. No. 5,441,193 to Gravener illustrates yet another attempt at producing a reinforced surgical fastener suture line. To accomplish the desired goal, a sheet of resilient material having a concave shape along the longitudinal axis is attached to one or both of the anvil and cartridge portions for biasing the subject body tissue together when the anvil and cartridge portions of the surgical fastener applying device are closed onto the body tissue. A disadvantage exists with this arrangement, however, in that a great amount of care must be taken to ensure that the curved resilient sheet is positioned appropriately on the anvil and cartridge portions. The positioning of the curved resilient sheet is particularly important because the apex or center of the curved undersurface must be aligned directly in the plane of the surgical fasteners to ensure optimal performance. To be more specific, improper alignment may cause the surgical fasteners to penetrate the resilient material off the centerline of the curved undersurface and thus reduce the ability of the curved material to effectively bias the subject body tissue. Individuals having a modicum of skill in the art will recognize and appreciate that such an inability to bias the subject body tissue may result in a surgical fastener suture line which is less than adequate in reducing fluid leakage and tissue tearing. This technique is also disadvantageous from the standpoint of cost due to the fact that the cartridges, anvils, and curved resilient material must be custom made and, moreover, due to the precise positioning required to secure the resilient material so that the apex of the curved undersurface is coplanar with each line of surgical fasteners and/or retaining elements disposed in the cartridge and anvil portions, respectively.

Yet another ill attempt at providing reinforced surgical fastener suture lines resides in U.S. Pat. No. 5,397,324 to Carroll et al. This reference discloses a surgical fastener applying device having a pair of flexible body-absorbable or non-absorbable pads which are captively held on the fastener cartridge during the positioning of the subject body tissue between the anvil and fastener cartridge and releasable such that the surgical fasteners upon ejection from the cartridge will penetrate through the pads, the tissue, and bend against the anvil. However, a substantial drawback exists with this arrangement in that the flexible pads are captively and releasibly held in a channel having the shape of a key-way slot which is bounded in part by the anvil engagement face of the fastener cartridge and a pair of overhanging arm members having axially extending lips which are laterally spaced apart for holding the pads. While this method of attachment does effectively allow the flexible pad to release from the anvil upon the firing of the surgical fastener applying device, this arrangement is nonetheless disadvantageous due to the custom manufacturing which must be undertaken to produce fastener cartridges having the overhanging arms. This custom manufacturing increases the cost of implementing such a device and method. Furthermore, it also limits the number of surgical fastener applying devices which can retrofitted to employ and exploit this technology.

U.S. Pat. No. 5,503,638 to Cooper et al. represents still another effort to produce reinforced surgical fastener suture lines. Here it is taught to provide a U-shape buttress member having pledget material removably affixed between the parallel sides of the buttress member via filament stitching. The placement of the pledget material on the sides of the U-shaped buttress forms a longitudinal lumen which is dimensioned to slip over the fastener cartridge or the anvil such that the pledget material is maintained generally flush with the apposed surfaces of the cartridge and the anvil. The cartridge and anvil may then be compressed over a portion of body tissue and the surgical fastener applying device fired to drive the surgical fasteners through the pledget material and body tissue and thereby affix the pledget material to the body tissue. Following the sandwiching of the body tissue between the pledget material, the filament stitching is then removed so as to free the buttress from the pledget material, thereby allowing the buttress and any excised disease tissue to be removed from the patient prior to closing. The buttress member of this invention may be formed in any particular size such that this technique is highly effective in preparing any type of surgical fastener applying device with pledget material to produce reinforced surgical fastener suture lines. However, this technique requires the steps of removing the stitching and the buttress member after the surgical fasteners have been applied to the body tissue.

A need therefore exists for a device and method for producing reinforced suture lines which overcomes the aforementioned deficiencies in the prior art. To be more specific, a device and method for producing reinforced surgical fastener suture lines is needed which does not require custom-made surgical fasteners and/or custom-made surgical fastener applying devices, thereby eliminating expense. This device and method should also veer away from requiring any increase in the number of surgical fasteners within a given area, thereby minimizing the burdens associated with aligning the surgical fasteners in the cartridge with the fastener-closing depressions and/or interlocking retaining elements in the anvil. A need also exists for a device and method for producing reinforced suture lines which does not require the size of the instrument to increase, thereby allowing the technique to have universal applicability with any type and size of surgical fastener applying device. It is a still further need to produce such a device and method which is capable of being used to retrofit surgical fastener applying devices having both disposable and non-disposable anvils and cartridges. There is also a need for a device and method which does not require custom made disposable anvil and cartridges, thereby reducing the costs of producing reinforced surgical fastener suture lines. It would also be desirable to produce such a device and method which does not require ultra precise positioning of the pledget material onto the cartridge and/or anvil. Finally, it would be advantageous to produce a device and method for producing reinforced surgical fastener suture lines which does not require the use of stitching to maintain the pledget material over the anvil and cartridge nor the use of a buttress member which must be removed from the surgical site following the application of the fasteners.

SUMMARY OF THE INVENTION

It is accordingly a principal object of the present invention to provide a device and method for producing reinforced surgical fastener suture lines which does not require custom-made surgical fasteners and/or custom-made surgical fastener applying devices, thereby eliminating expense.

It is a further object of the present invention to provide a device and method for producing reinforced surgical fastener suture lines which does not require an increase in the number of surgical fasteners within a given area, thereby minimizing the burdens associated with aligning the surgical fasteners in the cartridge with the fastener-closing depressions and/or interlocking retaining elements in the anvil.

It is yet another object of the present invention to provide a device and method for producing reinforced surgical fastener suture lines which is universal in applicability irrespective of the size of the surgical fastener applying device, thereby allowing the present invention to be used on any type and size of surgical fastener applying device from the more bulky medical staplers to smaller instruments for use in minimally invasive laparoscopic procedures.

It is still another object of the present invention to provide a device and method for producing reinforced surgical fastener suture lines which is capable of retrofitting surgical fastener applying devices having both disposable and non-disposable anvils and cartridges.

It is yet another object of the present invention to provide a device and method for producing reinforced surgical fastener suture lines which does not require custom made disposable anvil and cartridges, thereby reducing the costs associated with providing an improved and fortified surgical fastener suture line.

It is another object of the present invention to provide a device and method for producing reinforced surgical fastener suture lines which functions properly regardless of the exact alignment between an article of pledget material and the individual rows of surgical fasteners and/or retaining members of the fastener cartridge and anvil portions.

It is still another object of the present invention to provide a device and method for producing reinforced surgical fastener suture lines which maintains the pledget material in position next to the cartridge and/or anvil without the use of stitching or the use of a buttress member which must be removed from the surgical site following the application of the fasteners.

In accordance with the present invention, the foregoing objects and advantages are achieved by providing an apparatus for equipping a surgical fastener applying device to provide reinforced surgical fastener suture lines, comprising alignment means, pressure equalization means, and at least one article of pledget material. The alignment means has at least one guide channel and a receiving area, wherein the at least one guide channel is disposed in communication with the receiving area. The pressure equalization means is disposed within the receiving area of the alignment means. The at least one article of pledget material is disposed within the receiving area in juxtaposed relation with the pressure equalization means and positioned so as to be generally co-aligned with the at least one guide channel.

In accordance with another broad aspect of the present invention, the aforementioned objects are attained by providing a surgical kit for facilitating application of an article of pledget material to the apposed working surfaces of a surgical fastener applying device for producing reinforced surgical fastener suture lines, comprising alignment means, at least one article of pledget material, pressure equalization means, and means for temporarily securing the at least one article of pledget material to the working surface of the surgical fastener applying device. The at least one article of pledget material has a shape that generally complements the shape of the working surface of the surgical fastener applying device. The pressure equalization means is disposed in the alignment means for supporting and equalizing the pressure applied to the at least one article of pledget material during contact with the working surface of the surgical fastener applying device.

In yet another broad aspect of the present invention, an apparatus for producing reinforced surgical fastener suture lines is provided comprising retainer means and means for releasibly attaching at least one article of pledget material to a working surface of a surgical fastener applying device. The retainer means has means for retaining at least one article of pledget material and means for guiding a working surface of a surgical fastener applying device into contact with the at least one article of pledget material.

In a still further broad aspect of the present invention, a method of retrofitting surgical fastener applying devices to produce reinforced surgical fastener suture lines is provided wherein the surgical fastener applying device has a pair of apposed working surfaces, the method comprising the steps of: (a) providing retaining means for releasibly retaining an article of pledget material in physical contact with pressure equalization means; (b) providing means for releasibly attaching the article of pledget material to one of the pair of apposed working surfaces of the surgical fastener applying device; and (c) releasibly attaching the article of pledget material on one of the pair of apposed working surfaces of the surgical fastener applying device.

The foregoing features and advantages of the present invention will be readily apparent to those skilled in the art from a review of the following detailed description of the preferred embodiment in conjunction with the accompanying drawings and claims.

DETAILED DESCRIPTION OF THE PREFERRED EMBODIMENTS

Figure 1A:
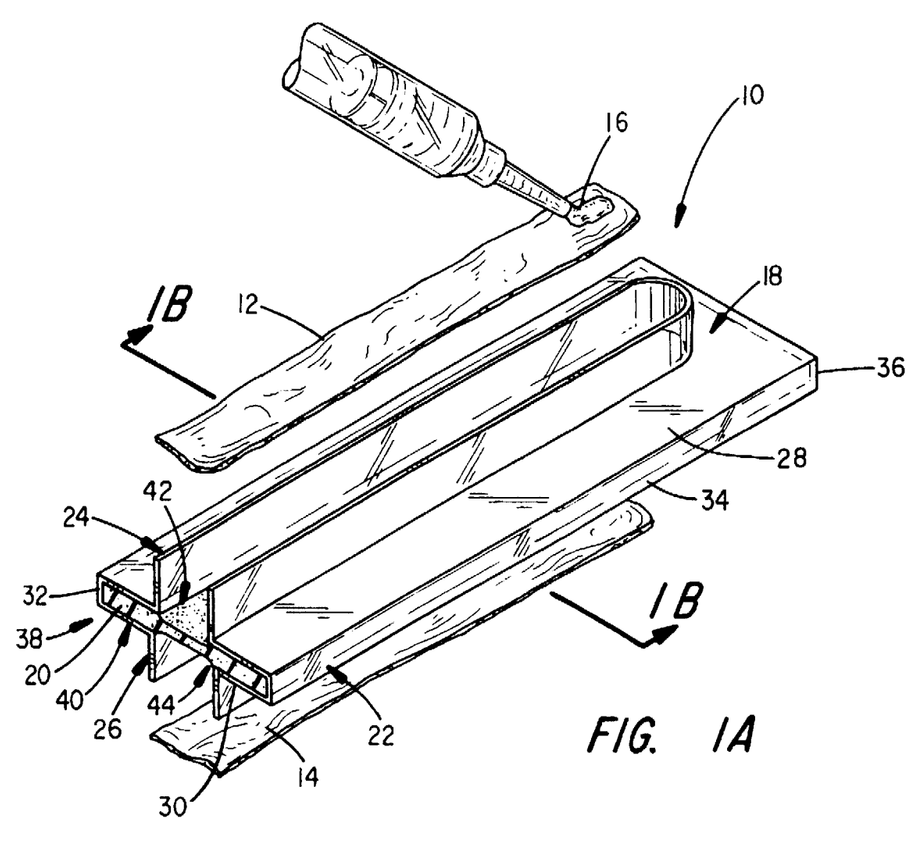
FIG. 1A is a partially exploded perspective view of an apparatus for producing reinforced surgical fastener suture lines of a first preferred embodiment of the present invention, including a retainer assembly 10, a first article of pledget material 12 to be disposed within a first guide channel 24 of an alignment frame 18, a second article of pledget material 14 to be disposed within a second guide channel 26 of the alignment frame 18, and an adhesive 16 for temporarily attaching the first and second articles of pledget material 12, 14 to the apposed working surfaces of a surgical fastener applying device.

Referring first to FIG. 1A, shown is a partially exploded view of an apparatus for producing reinforced surgical fastener suture lines in accordance with a first preferred embodiment of the present invention. More specifically, the apparatus of the present invention includes a retainer assembly 10, a first article of pledget material 12, a second article of pledget material 14, and an adhesive 16. In a preferred embodiment of the present invention, the first and second articles of pledget material 12, 14 comprise treated bovine pericardium available from the applicant's assignee and sold under its trademarks PERI-GUARD® and SUPPLE PERI-GUARD™. The use of this particular type of material is advantageous in that it has a much higher density of collagen than most other connective tissues and is cross linked with glutaraldehyde. The high density of the bovine pericardium provides increased structural integrity about the surgical fastener suture line and decreases the degree to which the pledget material will distend around the surgical fasteners. The cross linking with glutaraldehyde is advantageous in that it decreases the antigenicity of the tissue, thereby resulting in little or no inflammatory reaction with the adjoining body tissue. While the preferred embodiment of the present invention employs bovine pericardium as the first and second articles of pledget material 12, 14, it is to be readily understood that other suitable pericardium or dura mater may be employed, including but not limited to equine, porcupine, ovine, and human, as well as bio-compatible synthetic pledget materials.

By way of overview, the present invention accomplishes the goal of producing reinforced surgical fastener suture lines by equipping the jaw members of a surgical fastener applying device with the first and second articles of pledget material 12, 14 such that, when clamped about a portion of body tissue and fired, the surgical fastener applying device will fixedly attach the first and second articles of pledget material 12, 14 between a plurality of surgical fasteners and the subject body tissue. Positioning the first and second articles of pledget material 12, 14 in this fashion effectively minimizes the degree to which fluid leakage and/or tissue tearing occurs along the suture line. The propensity for fluid leakage is reduced in that the first and second articles of pledget material 12, 14 provide a more uniform distribution of pressure along the surgical fastener suture line, thereby increasing the contact area between the compressed portions of body tissue. The propensity for tissue tearing is also reduced because the first and second articles of pledget material 12, 14 provide added structural support between the subject body tissue and the surgical fasteners, thereby reducing the tendency of the individual surgical fasteners to tear through diseased and/or weakened body tissue. As will be discussed in greater detail below, the present invention is designed for use with any number of surgical fastener applying devices, including but not limited to those having pivotally related jaw members, such as those disclosed in U.S. Pat. No. 4,354,628 to Green and U.S. Pat. No. 5,141,144 to Foslien et al., and those having linearly translatable jaw members, such as those disclosed in U.S. Pat. No. 4,568,009 to Green and U.S. Pat. No. 4,508,253 to Green.

Figure 1B:
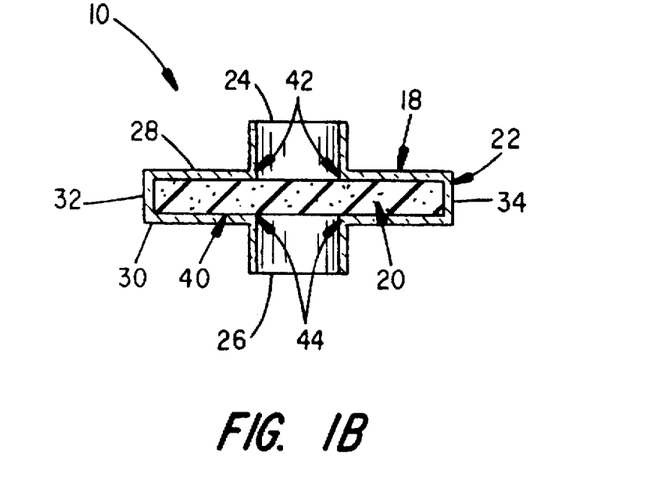
FIG. 1B is a cross sectional view of the retainer assembly 10 taken along line 1B—1B in FIG. 1A, including an alignment frame 18 having a receiving area 40 disposed between the first and second guide channels 24, 26, and a pressure equalization member 20 disposed within the receiving area 40 of the alignment frame 18.

The present invention is capable of equipping any of the aforementioned surgical fastener applying devices to produce reinforced suture lines by disposing the first and second articles of pledget material 12, 14 in releasable attachment within the retainer assembly 10 such that the first and second articles of pledget material 12, 14 will be automatically lined up with the apposed jaw members of a surgical fastener applying device. Referring collectively to FIGS. 1A and 1B, this is accomplished by providing the retainer assembly 10 to include an alignment frame 18 and an internally disposed pressure equalization member 20. The alignment frame 18 includes a generally planar sheath portion 22, a first guide channel 24, and a second guide channel 26. Sheath portion 22 includes a generally planar upper member 28, a generally planar lower member 30, a first side wall member 32, a second side wall member 34, and an end wall member 36. Upper member 28 and lower member 30 are substantially identical in construction and integrally connected to the first side wall member 32, the second side wall member 34, and the end wall member 36 so as to define an open end 38 opposite the end wall member 36. First side wall member 32, second side wall member 34, and end wall member 36 are substantially equal in height such that upper member 28 and lower member 30 extend generally parallel to one another to define an internally disposed receiving area 40 that extends laterally between the interior surfaces of the first and second side wall members 32, 34, vertically between the plane of the interior surface of the upper member 28 and the plane of the interior surface of the lower member 30, and longitudinally between the interior surface of end wall member 36 and the plane of the open end 38.

The first guide channel 24 and the second guide channel 26 extend from the upper and lower members 28, 30, respectively, of the sheath portion 22 and are dimensioned to regulate the engagement of the apposed working surfaces of a surgical fastener applying device and the retainer assembly 10. More particularly, the first guide channel 24 extends generally perpendicularly from a first coupling aperture 42 formed within the upper member 28, while the second guide channel 26 extends generally perpendicularly from a second coupling aperture 44 formed within the lower member 30. As will be described in greater detail below, the first and second articles of pledget material 12, 14 are to be positioned within the receiving area 40 in general alignment with the first and second coupling apertures 42, 44, respectively, such that the first and second guide channels 24, 26 will automatically direct the apposed working surfaces of a surgical fastener applying device into contact with the first and second articles of pledget material 12, 14 when the surgical fastener applying device is clamped down onto the retainer assembly 10. This effectively ensures for a consistent method of engagement between the particular surgical fastener applying device and the retainer assembly 10 such that the first and second articles of pledget material 12, 14 will always be applied to the apposed working surfaces of the surgical fastener applying device in the desired and proper manner. This advantageously allows a physician to quickly and easily retrofit a prior art surgical fastener applying device to produce reinforced suture lines without undertaking painstaking efforts to properly position the pledget material on the surgical fastener applying device, thereby minimizing the costs associated with producing fortified surgical fastener suture lines.

In the preferred embodiment shown, the pressure equalization member 20 is formed having substantially the same dimensions as the aforementioned receiving area 40 such that the pressure equalization member 20 is capable of being slidably received within the receiving area 40. In this arrangement, at least a portion of the pressure equalization member 20 is exposed through the first and second coupling apertures 42, 44 when the pressure equalization member 20 is disposed within the receiving area 40. The pressure equalization member 20 is preferably constructed from a deformable yet resilient substrate, such as foam plastic, rubber, and/or any number of suitable materials having similar properties. As will be described further below, the deformable and resilient nature of the pressure equalization member 20 is particularly important to the present invention in that it provides for a more even distribution of pressure between the apposed working surfaces of a surgical fastener applying device and the first and second articles of pledget material 12, 14, respectively, when the surgical fastener applying device is closed to force the apposed working surfaces thereof into contact with the first and second articles of pledget material 12, 14, respectively. By providing such a uniform distribution of pressure, the pressure equalization member 20 ensures that the first and second articles of pledget material 12, 14 will more readily conform to the shape and contour of the apposed working surfaces during the step of closing the surgical fastener applying device about the retainer assembly 10. The resiliency of the pressure equalization member 20 is also advantageous in that it serves to releasibly bias the first and second articles of pledget material 12, 14 within the receiving area 40 of the alignment frame 18.

As mentioned above, the first and second articles of pledget material 12, 14 are designed to be positioned within the receiving area 40 so as to be generally in line with the first and second guide channels 24, 26, respectively. Arranged as such, the first and second articles of pledget material 12, 14 will be automatically lined up with the apposed jaw members of a surgical fastener applying device when the surgical fastener applying device is registered within the first and second guide channels 24, 26, respectively. The first and second articles of pledget material 12, 14 are retained within the alignment frame 18 by forming the first and second articles of pledget material 12, 14 so that each has a peripheral boundary which is slightly larger than the first and second coupling apertures 24, 26, respectively. In other words, the first and second articles of pledget material 12, 14 are designed such that the outer peripheral edges thereof are capable of extending past the first and second coupling apertures 42, 44, respectively. When positioned within the receiving area, then, the outer peripheral edges of the first and second articles of pledget material 12, 14 are sandwiched between the pressure equalization member 20 and the interior surfaces of the upper and lower members 28, 30 of the sheath portion 22. This sandwiching, once again, is due to the resiliency of the pressure equalization member 20, which exerts a biasing force against the peripheral edges of the first and second articles of pledget material 12, 14 to effectively retain the first and second articles of pledget material 12, 14 within the retainer assembly 10. In this configuration, therefore, the retainer assembly 10 includes the alignment frame 18 with the pressure equalization member 20 disposed therewithin.

In order to equip a surgical fastener applying device to produce reinforced surgical fastener suture lines in accordance with the present invention, means must be provided to form a releasable bond between the first and second articles of pledget material 12, 14 and the apposed working surfaces of the surgical fastener applying device such that the first and second articles of pledget material 12, 14 may be removed from the retainer assembly 10 and temporarily positioned on the apposed working surfaces of the surgical fastener applying device. In the preferred embodiment shown, this is accomplished through the use of the adhesive 16 which is applied to the outwardly facing surfaces of the first and second articles of pledget material 12, 14. Following the application of an effective amount of adhesive 16, the apposed working surfaces of the surgical fastener applying device are positioned within the first and second guide channels 24, 26, respectively, and clamped down into contact with the adhesive-laden first and second articles of pledget material 12, 14. The surgical fastener applying device is maintained in this closed position for a given period of time and then pulled away from the alignment frame 18 to remove the pressure equalization means 20, along with the first and second articles of pledget material 12, 14, from within the receiving area 40. The adhesive 16 forms a sufficient bond between the first and second articles of pledget material 12, 14 and the apposed working surfaces of the surgical fastener applying device such that, when the surgical fastener applying device is opened from the previously clamped position, the first and second articles of pledget material 12, 14 remain releasably attached to the apposed working surfaces of the surgical fastener applying device and the pressure equalization member 20 may be removed from between the first and second articles of pledget material 12, 14. The surgical fastener applying device is then fully equipped with the first and second articles of pledget material 12, 14 such that the apposed working surfaces thereof may be positioned about a section of body tissue to form a reinforced surgical fastener suture line in accordance with the present invention.

In the preferred embodiment of the present invention, the adhesive 16 is a tacky liquid substance which may include, but is not necessarily limited to, hydroxypropylmethyl cellulose, propylene glycol, and water. Due to the liquid nature, the adhesive 16 is to be applied to the first and second articles of pledget material 12, 14 while the first and second articles of pledget material 12, 14 are retained within the receiving area 40 immediately prior to the particular medical procedure. When used in conjunction with treated bovine pericardium, the use of such a tacky liquid substance serves several important functions. First, the water within the adhesive 16 is drawn into the treated bovine pericardium, thereby increasing the pliability and flexibility of the first and second articles of pledget material 12, 14. This allows the first and second articles of pledget material 12, 14 to more readily conform to the shape and contours of the apposed working surfaces when the surgical fastener applying device is clamped down onto the first and second articles of pledget material 12, 14. Another benefit to using a liquid-based adhesive is that, by softening the first and second articles of pledget material 12, 14, the adhesive 16 reduces the likelihood that the first and second articles of pledget material 12, 14 will experience cracking when surgical fasteners are forced to penetrate therethrough.

Figure 2A:
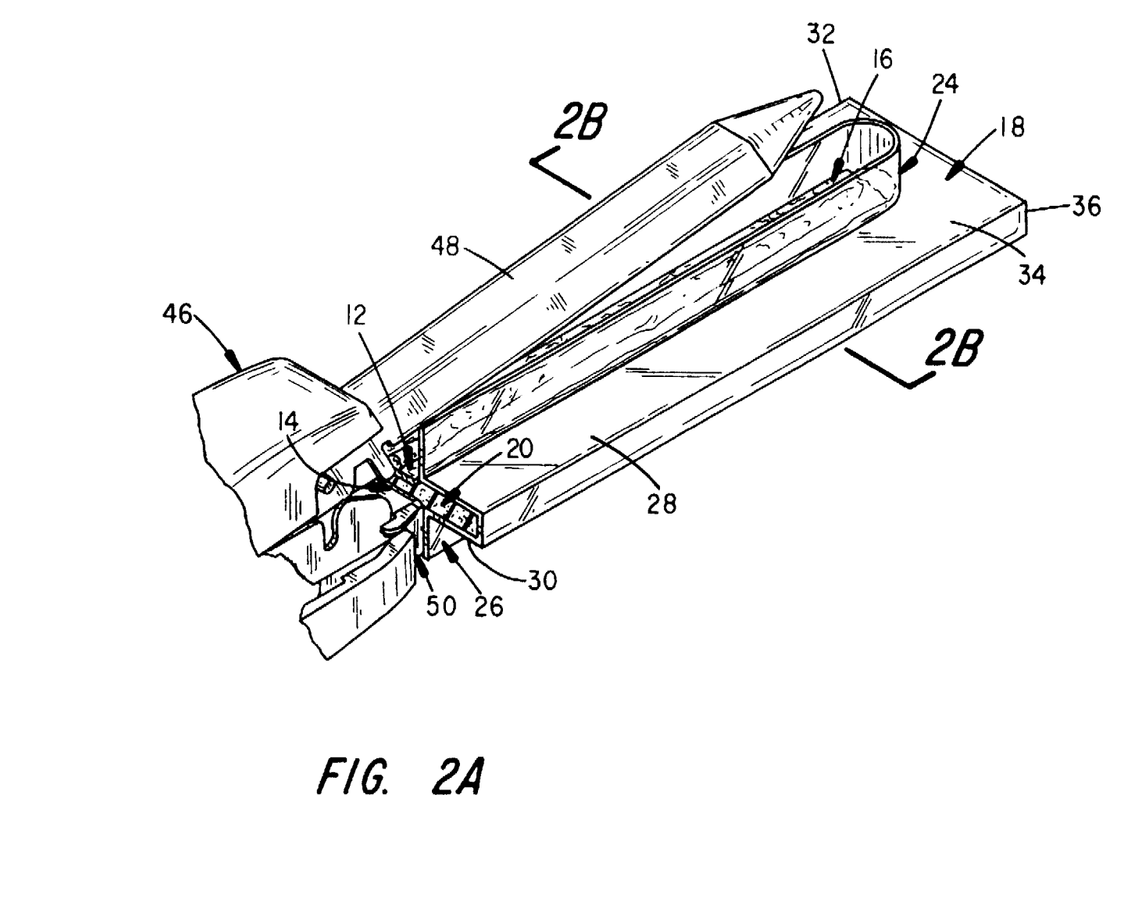
FIG. 2A is a perspective view illustrating the method of engagement between a typical surgical fastener applying device 46 and the retainer assembly 10, wherein the first and second articles of pledget material 12, 14 are disposed within the first and second guide channels 24, 26, respectively, in accordance with the first preferred embodiment of the present invention.
Figure 2B:
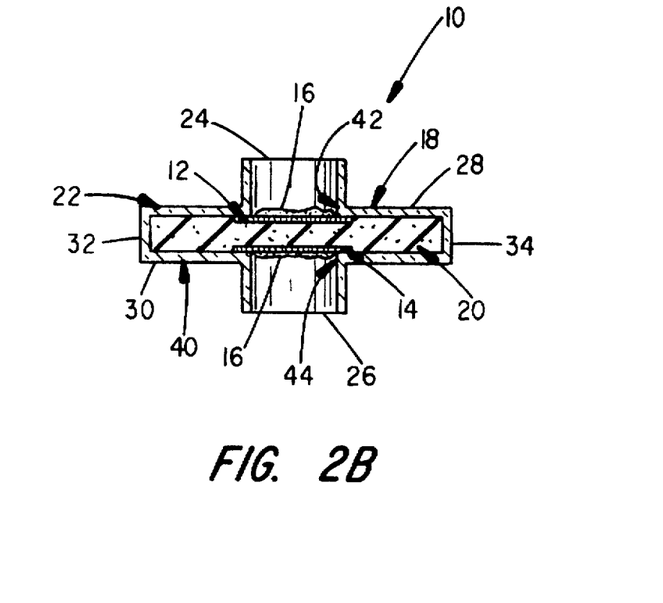
FIG. 2B is cross sectional view of the retainer assembly 10 taken along line 2B—2B in FIG. 2A with the first and second articles of pledget material 12, 14 disposed within the first and second guide channels 24, 26, respectively, in accordance with the first preferred embodiment of the present invention.

With reference now to FIGS. 2A and 2B, the present invention is shown fully enabled for use with a surgical fastener applying device 46. In this condition, the first and second articles of pledget material 12, 14 are releasibly disposed within the receiving area 40 so as to be generally aligned with the first and second guide channels 24, 26, respectively. More specifically, the first article of pledget material 12 is positioned longitudinally within the receiving area 40 such that the periphery thereof is sandwiched between the pressure equalization member 20 and the interior surface of the upper member 28 of the sheath portion 22, while the second article of pledget material 14 is similarly positioned within the receiving area 40 such that the periphery thereof is sandwiched between the pressure equalization member 20 and the interior surface of the lower member 30 of the sheath portion 22. The adhesive 16 is applied to the exposed, outwardly facing surfaces of the first and second articles of pledget material 12, 14. In this arrangement, the surgical fastener applying device 46 may be simply and quickly equipped to provide reinforced suture lines by: (1) engaging the first and second jaw members 48, 50 within the first and second guide channels 24, 26, respectively; (2) clamping the first and second jaw members 48, 50 together so as to compress the first and second articles of pledget material 12, 14 into contact with the pressure equalization member 20; (3) removing the pressure equalization member 20 and the first and second articles of pledget material 12, 14 from within the receiving area 40 by pulling the surgical fastener applying device and the alignment frame 18 away from one another; and (4) opening the surgical fastener applying device 46 such that the first and second articles of pledget material 12, 14 are temporarily attached to the apposed working surfaces of the first and second jaw members 48, 50, respectively.

In a typical configuration, the first jaw member 48 will be equipped with a fastener cartridge having at least two laterally spaced rows of fasteners, while the second jaw member 50 will be furnished with an anvil having fastener-closing depressions and/or interlocking retaining elements aligned with the rows of fasteners in the cartridge. The surgical fasteners employed may include, but are not necessarily limited to, conventional staples and/or two-piece interlocking fasteners constructed from metal and/or non-metallic resinous material. When using with conventional staples, the present invention ensures that the surgical fastener applying device 46 will drive the staple legs through the first article of pledget material 12, the subject body tissue, and the second article of pledget material 14 before being cinched by depressions formed in the second jaw member 50 to thereby secure the first and second articles of pledget material 12, 14 on either side of the subject body tissue. With regard to two-piece surgical fasteners, the present invention will similarly ensure that the legs of the fasteners will be driven through the first article of pledget material 12, the subject body tissue, and the second article of pledget material 14 before being interlocked with retainer members disposed within the second jaw member 50 to secure the first and second articles of pledget material 12, 14 about the compressed body tissue. As such, the surgical fastener applying device 46 may create a reinforced surgical fastener suture line by simply closing the first and second jaw members 48, 50 upon a portion of body tissue and firing the surgical fastener applying device 46 to drive fasteners from the first jaw member 48 to sandwich a portion of body tissue between the first and second articles of pledget material 12, 14.

The relatively simple construction of the present invention is advantageous in that it provides the ability to load the first and second articles of pledget material 12, 14 within the retainer assembly 10 in one of several quick and easy fashions. For example, the first and second articles of pledget material 12, 14 may be loaded at the same time the pressure equalization member 20 is being inserted into the receiving area 40 of the alignment frame 18 or, alternatively, the first and second articles of pledget material 12, 14 may be loaded subsequent to the insertion of the pressure equalization member 20 into the alignment frame 18. The first and second articles of pledget material 12, 14 may be loaded at the same time the pressure equalization member 20 is being inserted into the alignment frame 18 by simply positioning the first and second articles of pledget material 12, 14 on either side of the pressure equalization member 20 and sliding this entire combination into the receiving area 40 such that the first and second articles of pledget material 12, 14 are generally co-aligned with the first and second guide channels 24, 26, respectively. The first and second articles of pledget material 12, 14 may be positioned within the retainer assembly 10 after the pressure equalization member 20 has been disposed within the alignment frame 18 by simply tucking the peripheral edges of the first and second articles of pledget material 12, 14 in between the pressure equalization member 20 and the interior surfaces of the upper and lower members 28, 30, respectively, of the alignment frame 18 such that the first and second articles of pledget material 12, 14 are generally co-aligned with the first and second guide channels 24, 26, respectively.

In an important aspect of the present invention, the first and second articles of pledget material 12, 14 are capable of being generally co-aligned with the first and second guide channels 24, 26, respectively, regardless of the particular loading scenario employed. This is made possible by deliberately sizing the first and second articles of pledget material 12, 14 to have larger peripheral edges than the peripheral edges of the first and second coupling apertures 42, 44, respectively. Stated another way, the first and second articles of pledget material 12, 14 are both formed having a predetermined width and length that exceed the length and width of the first and second coupling apertures 42, 44. The main benefit to providing the first and second articles of pledget material 12, 14 with a larger peripheral shape than the first and second coupling apertures 42, 44, respectively, is that this effectively decreases the degree of precision which must be used when positioning the first and second articles of pledget material 12, 14 within the receiving area 40. This reduced sensitivity to precise positioning stems from the fact that the extra width and length allows the first and second articles of pledget material 12, 14 to be positioned slightly askew from the centerline of the coupling apertures 42, 44 without jeopardizing the ability of the pressure equalization member 20 to bias the first and second articles of pledget material 12, 14 into contact with the sheath portion 22 of the alignment frame 18. This advantageously reduces the amount of time and labor which must be expended to prepare the retainer assembly 10 with the first and second articles of pledget material 12, 14, thereby minimizing the overall cost of the present invention.

Figure 3A:
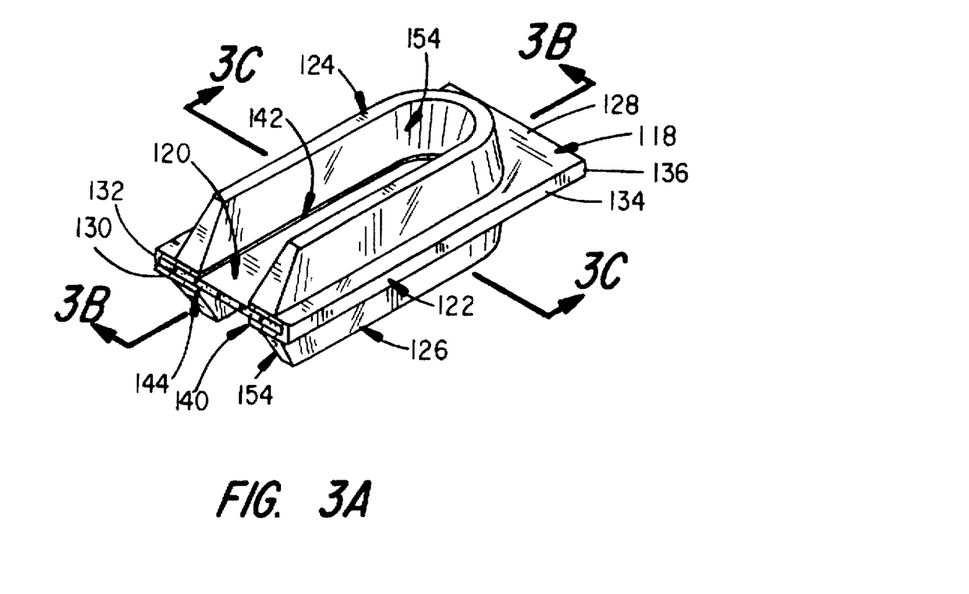
FIG. 3A is a perspective view illustrating a retainer assembly 110 of a second preferred embodiment of the present invention, including an alignment frame 118 having a first beveled guide channel 124, a second beveled guide channel 126, and a receiving area 140 disposed therebetween, and a pressure equalization member 120 disposed within the receiving area 140 of the alignment frame 118.
Figure 3B:
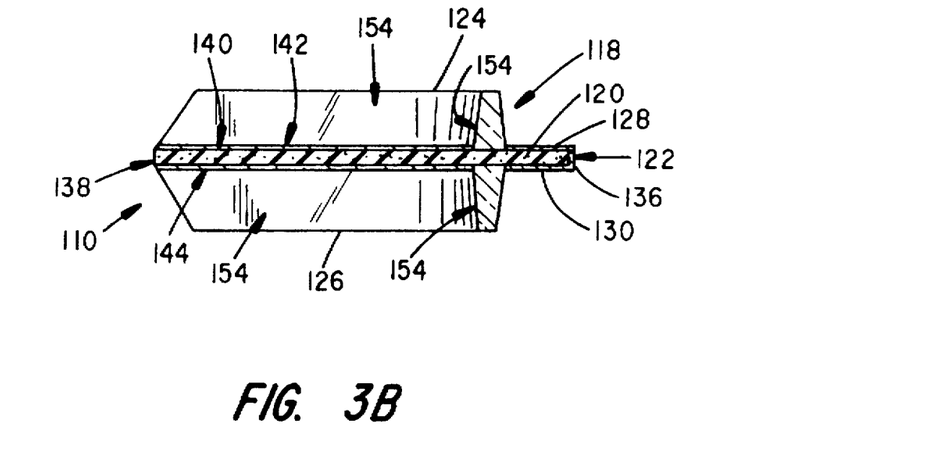
FIG. 3B is a cross sectional view of the retainer assembly 110 taken along line 3B—3B in FIG. 3A illustrating the angled nature of the first and second beveled guide channels 124, 126 and further detailing the position of the pressure equalization member 120 within the receiving area 140 of the alignment frame 118.
Figure 3C:
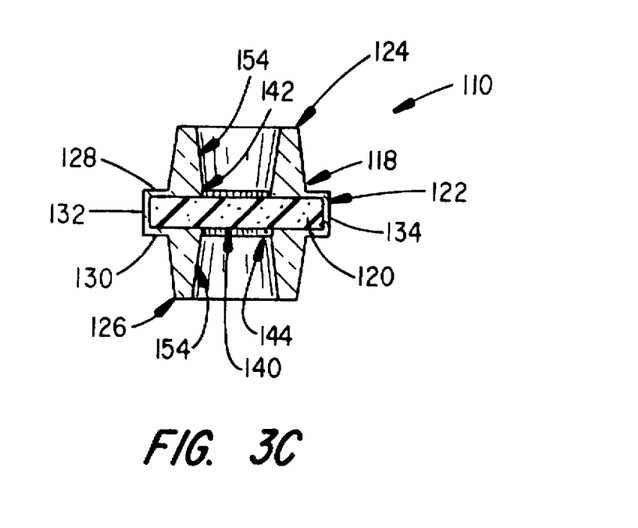
FIG. 3C is a cross sectional view of the retainer assembly 110 taken along line 3C—3C in FIG. 3A, further illustrating the angled nature of the first and second beveled guide channels 124, 126 and the position of the pressure equalization member 120 within the receiving area 140 of the alignment frame 118.

Referring now to FIGS. 3A-3C, illustrated is a retainer assembly 110 of a second preferred embodiment of the present invention. FIG. 3A shows the retainer assembly 110 in perspective, generally comprising an alignment frame 118 and a pressure equalization member 120. As with the first preferred embodiment, the alignment frame 118 of the second preferred embodiment includes a sheath portion 122, a first guide channel 124 extending generally perpendicularly from a first coupling aperture 142 formed in one side of the sheath portion 122, and a second guide channel 126 extending generally perpendicularly from a second coupling aperture 144 formed in the opposite side of the sheath portion 122. The sheath portion 122 includes a generally planar upper member 128, a generally planar lower member 130, a first side wall member 132, a second side wall member 134, and an end wall member 136 which combine to define a receiving area 140 for receiving the pressure equalization member 120 therewithin. The receiving area 140 extends laterally between the interior surfaces of the first and second side wall members 132, 134, vertically between the plane of the interior surface of the upper member 128 and the plane of the interior surface of the lower member 130, and longitudinally between the interior surface of end wall member 136 and the plane of an open end 138. Referring collectively to FIGS. 3A-3C, it can be seen that the pressure equalization member 120 is dimensioned to be slidably received within the receiving area 140. As will be discussed further below, the pressure equalization member 120 is constructed from a generally deformable and resilient material, such as foam, so as to exert a biasing force to maintain pledget material within the receiving area 140.

The only difference between the retainer assembly 110 of the second preferred embodiment shown in FIGS. 3A-4C and the retainer assembly 10 of the first preferred embodiment shown in FIGS. 1A-2B is the beveled nature of the first and second guide channels 124, 126. As can be seen, the first and second guide channels 124, 126 extend generally perpendicularly from the upper and lower members 128, 130, respectively, of the alignment frame 118. However, with particular reference to FIGS. 3B and 3C, the first and second guide channels 124, 126 each have an interiorly disposed engagement surface 154 which angles laterally outward as it extends away from the plane of the upper and lower members 128, 130, respectively. The alignment frame 118 is preferably constructed from a generally flexible yet resilient material, such as plastic, such that the first and second guide channels 124, 126 are capable of flexing laterally outward when the angled engagement surfaces 154 come into contact with the apposed jaw members of a surgical fastener applying device.

Figure 4A:
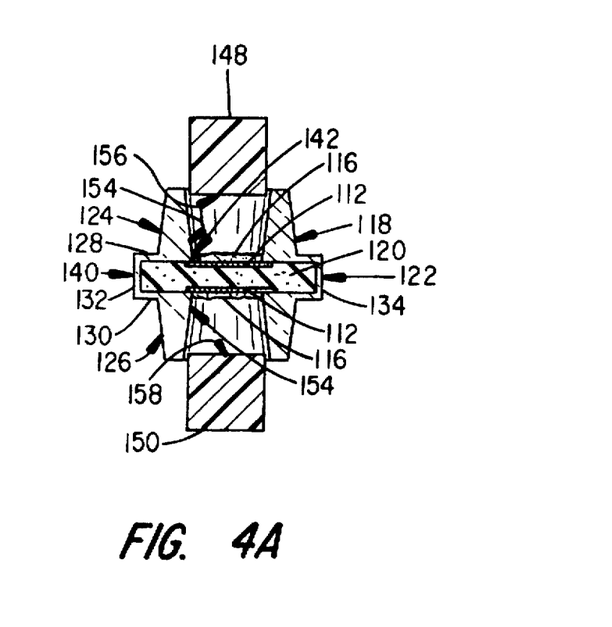
FIGS. 4A–4C are cross sectional views similar to that shown in FIG. 3C, illustrating the manner in which the first and second jaw members 148, 150 of a surgical fastener applying device engage with the first and second beveled guide channels 124, 126 to remove the first and second articles of pledget material 112, 114, respectively, from within the receiving area 140 in accordance with the second preferred embodiment of the present invention.
Figure 4B:
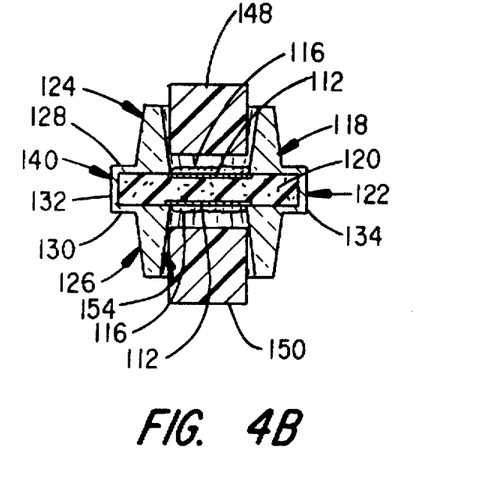
Figure 4C:
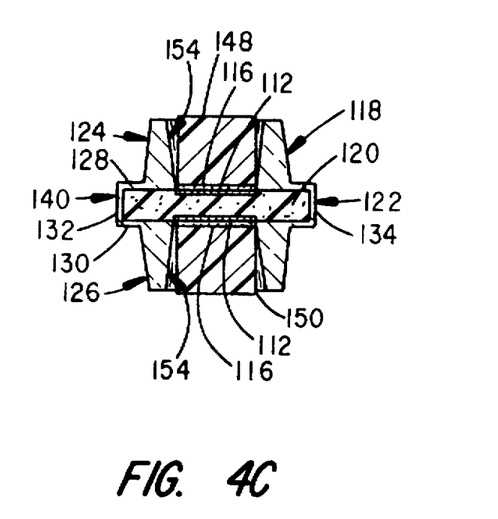

This feature can be best seen with reference to FIGS. 4A-4C, which depict the retainer assembly 110 of the second preferred embodiment of the present invention equipped with an adhesive 116 disposed on a first and a second article of pledget material 112, 114. Referring initially to FIG. 4A, it can be seen that the first and second guide channels 124, 126 are dimensioned to accept a first and a second jaw member 148, 150, respectively, of a surgical fastener applying device. More specifically, the alignment frame 118 is dimensioned such that the lateral edges of the first and second jaw members 148, 150 are capable of being receiving within the first and second guide channels 124, 126, respectively. In this arrangement, a working surface 156 of the first jaw member 148 is positioned generally parallel to the first article of pledget material 112, while a working surface 158 of the second jaw member 150 is positioned generally parallel to the second article of pledget material 114. FIGS. 4B and 4C illustrate the flexed response of the alignment frame 118 during the step of closing the first and second jaw members 148, 150 within the first and second guide channels 124, 126, respectively. As can be seen, the progressive clamping of the first and second jaw members 148, 150 toward the first and second articles of pledget material 112, 114 causes the first and second guide channels 124, 126 to distend laterally outward. This lateral distention progressively causes the first and second coupling apertures 142, 144 to widen to the point shown in FIG. 4C where the adhesive 116 is sandwiched between the working surfaces 156, 158 and the first and second articles of pledget material 112, 114, respectively, such that the first and second articles of pledget material 112, 114 are generally coaligned and flush with the working surfaces 156, 158. The first and second jaw members 148, 150 are further compressed and then pulled away from the alignment frame 118 with the pressure equalization member 120 clinched between the first and second articles of pledget material 112, 114. After the pressure equalization member 120 has been removed from within the receiving area 140, the jaw members 148, 150 are then opened and the pressure equalization member 120 removed from the previously described clinched position between the first and second articles of pledget material 112, 114. The adhesive 116 forms a bond sufficient to hold the first and second articles of pledget material 112, 114 on the apposed working surfaces 156, 158, respectively.

The present invention may be advantageously provided within a vacuum molded plastic container which is sterilized and hermetically sealed so as to provide the retainer assembly, the adhesive, and the articles of pledget material in a convenient and ready-to-use condition. In a preferred embodiment, the retainer assembly will be prepared at the manufacturing site with the pressure equalization member disposed within the receiving area of the alignment frame with the first and second articles of pledget material disposed within the first and second guide channels of the alignment frame. In this arrangement, the present invention can be quickly and efficiently employed to prepare a surgical fastener applying device for producing reinforced surgical fastener suture lines by carrying out the following steps: (1) Removing the retainer assembly from the sterile package; (2) Removing the adhesive tube from the sterile package; (3) Spreading the adhesive onto the first and second articles of pledget material as they are positioned within the first and second guide channels of the retainer assembly; (4) Positioning the apposed working surfaces of a surgical fastener applying device in general alignment with the first and second guide channels of the retainer assembly; (5) Closing the jaws of the surgical fastener applying device onto the adhesive-coated first and second articles of pledget material to compress the pressure equalization member; (6) Moving the surgical fastener applying device away from the alignment frame so as to remove the first and second articles of pledget material, with the pressure equalization member compressed therebetween, from within the receiving area of the alignment frame; (7) Opening the jaws of the surgical fastener applying device with the first and second articles of pledget material adhered to the apposed working surfaces thereof so as to remove the pressure equalization member from between the first and second articles of pledget material; (8) Positioning the apposed working surfaces of the surgical fastener applying device over a designated portion of body tissue; (9) Closing the jaw members of the surgical fastener applying device into a compressed relation about the subject body tissue; (10) Firing the surgical fastener applying device to form a reinforced surgical fastener suture line; (11) Opening the jaw members of the surgical fastener applying device; and (12) Removing the surgical fastener applying device from the site of the surgical fastener suture line.

In light of the foregoing, the present invention solves the various drawbacks found in the prior art. To be more specific, the present invention provides a device and method for producing reinforced surgical fastener suture lines which may be employed with any type of surgical fastener applying device, regardless of the type of surgical fasteners and/or the particular shape of the surgical fastener applying device. In this fashion, the present invention eliminates the need to create custom made surgical fasteners and/or custom made surgical fastener applying devices in order to form reinforced suture lines. The present invention also accomplishes the formation of reinforced surgical fastener suture lines without increasing the number of surgical fasteners within a given area, thereby minimizing the burdens associated with aligning the surgical fasteners in the cartridge with the fastener-closing depressions and/or interlocking retaining elements in the anvil. The present invention also does not require custom made disposable anvil and cartridges, thereby reducing the costs associated with providing an improved and fortified surgical fastener suture line. The present invention also does not require pledget material having curved biasing surfaces and, therefore, functions properly regardless of the exact alignment between an article of pledget material and the individual rows of surgical fasteners and/or retaining members of the fastener cartridge and anvil portions. Lastly, the present invention is capable of maintaining the pledget material in position next to the cartridge and/or anvil without the use of stitching or the use of a buttress member which must be removed from the surgical site following the application of the fasteners. Thus, the present invention offers wide versatility with a number of different surgical fastener applying devices to produce reinforced surgical fastener suture lines. The fortification of surgical fastener suture lines can serve many beneficial purposes, such as providing improved vascular hemostasis, and, in the case of a pneumectomy, overcoming the nature distension of the body tissue around the surgical fasteners to achieve total air occlusion.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

For example, although each alignment frame of the present invention is illustrated as a single article having fixed side and end wall members extending between the upper and lower members of the sheath portion, it is to be understood that the alignment frame may be formed from a plurality of separate interlocking and/or hingedly related pieces. To be more specific, it is contemplated to provide the alignment frame such that the guide channels and sheath portions are separate articles which may be selectively interlocked to produce a suitably sized alignment frame. In this regard, a kit may be provided including a plurality of sheath portions having differently sized receiving areas, a plurality of pressure equalization members to correspond to the various sheath portions, and a number of differently sized guide channels capable of being selectively interlocked with the various sheath portions. This would effectively allow a physician to quickly and easily form a plurality of differently sized retainer assemblies so as to accommodate any number of surgical fastener applying devices. In similar fashion, it is fully anticipated to form the alignment frame such that the upper and lower members of the sheath portion are hingedly related at either of the lateral sides or along the end wall. In such an arrangement, the upper and lower members of the sheath portion may be selectively closed together to enclose pledget material in a receiving area formed therebetween.

Moreover, notwithstanding the fact that the preferred embodiment described above calls for a liquid-based adhesive to be applied immediately prior to using the retainer assembly, it is to be readily understood that a wide variety of different adhesives may be employed, including but not limited to contact adhesives, such as polyacrylamides and natural gum rubbers applied during the manufacturing process, and hydrogels and other similar compounds which may be applied at the time of use. With specific regard to those adhesives applied during the manufacturing process, it is also contemplated to provide a protective film or covering over the adhesive layer to maintain the pledget material sterile prior to use. The use of such a protective film may also reduce the amount of time required to prepare the retainer assembly for use in that the user would not have to spend time manually applying the adhesive to the first and second articles of pledget material as described above. Rather, the user could simply peel away the protective film so as to avail the adhesive layers of the first and second articles of pledget material in order to prepare the retainer assembly for use.

It is also contemplated that the first and second articles of pledget material may be temporarily attached to the surgical fastener applying device by applying the adhesive directly to the working surfaces of the first and second jaw members. In this arrangement, the surgical fastener may then be closed about the retainer assembly to form the requisite temporary bond between the working surfaces of the jaw members and the pledget material such that the surgical fastener applying device may be thereafter opened and the pledget material removed from the retainer assembly.

In a similar fashion, it is conceivable to provide the jaw members of the surgical fastener applying device with other means for releasibly adhering the pledget material to the working surfaces. For instance, it is possible to design the jaw members with pneumatic suction capability such that a suction bond forms between the pledget material and the working surfaces of the jaw members when the surgical fastener applying device is closed onto the retainer assembly. This could be accomplished by providing an air line in fluid communication with the working surface of each jaw members and drawing air into the plane defined by the working surface of each jaw member in an amount sufficient to form a bond between the working surfaces of the jaw members and the pledget material that can overcome the resilient biasing force exerted by the pressure equalization member when the pledget material is disposed within the retainer assembly.

Figure 5:
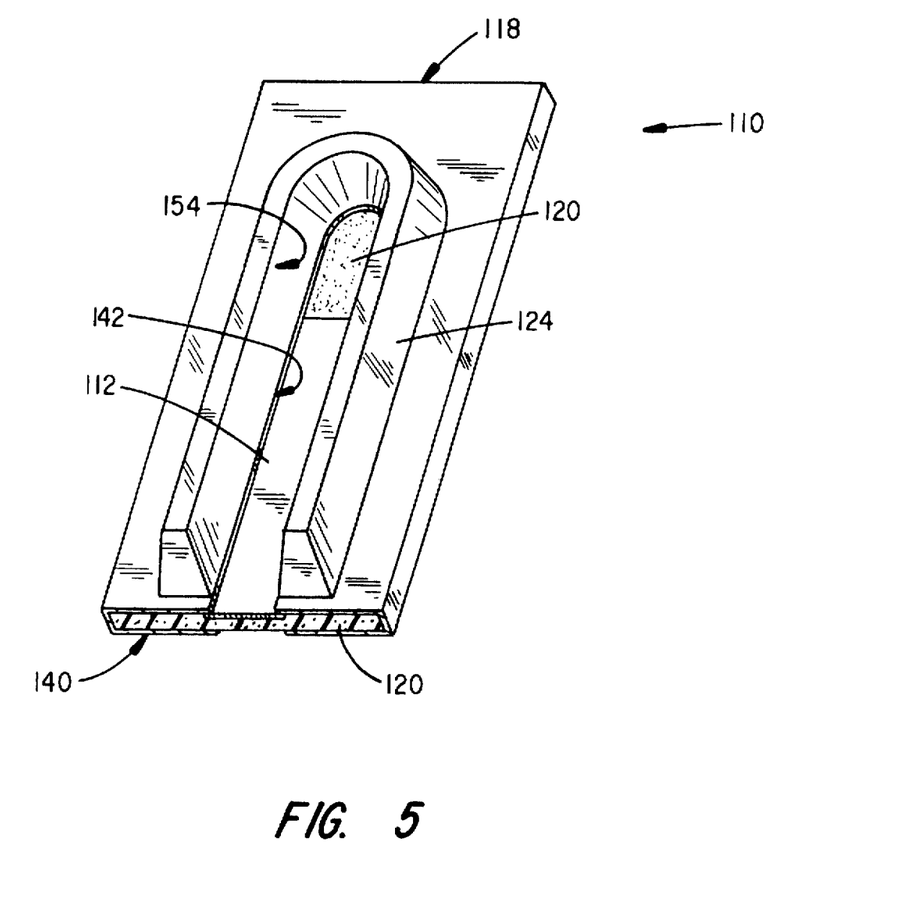
FIG. 5 is a perspective view of an alternate embodiment of the present invention, illustrating the retainer assembly 110 equipped with a single article of pledget material 112 having a length shorter than the length of the coupling aperture 142.

With reference to FIG. 5, it is also fully contemplated to equip the retainer assembly 110 of the present invention with a single article of pledget material 112 disposed within the first guide channel 126 to equip one of the jaw members of a surgical fastener applying device to produce a reinforced surgical fastener suture line. It is also fully anticipated to manufacture the article of pledget material 112 having a length shorter than the length of the coupling aperture 142 such that the working surface of the jaw member of the surgical fastener applying device will be partially covered with the article of pledget material 112. This, of course, translates to the first embodiment shown in FIGS. 1A–2B, as well as the second embodiment shown in FIGS. 3A–4C. In both embodiments, then, the articles of pledget material would still have width dimensions which exceed the width of the first and second coupling apertures, respectively, such that the first and second articles of pledget material may be properly positioned within the receiving area.

Moreover, although the preferred embodiment of the present invention entails constructing the alignment frame from plastic and related materials, it is to be understood that any number of metallic and/or ceramic substances may also be used to form the alignment frame without departing from the scope of the present invention.

What is claimed is:

1. An apparatus for equipping a surgical fastener applying device to provide reinforced surgical fastener suture lines, comprising:
    (a) a alignment means having at least one guide channel and a receiving area, said at least one guide channel being open to said receiving area;
    (b) pressure equalization means disposed within said receiving area of said alignment means; and
    (c) at least one article of pledget material disposed within said receiving area in juxtaposed relation with said pressure equalization means and positioned so as to be generally co-aligned with said at least one guide channel.

2. The apparatus as set forth in claim 1 and further, said alignment means comprising a sheath portion having at least one coupling aperture from which said at least one guide channel extends generally perpendicularly therefrom.

3. The apparatus as set forth in claim 2 and further, said at least one coupling aperture having the same approximate width and length of a working surface of said surgical fastener applying device.

4. The apparatus as set forth in claim 3 and further, said at least one guide channel being dimensioned to guide said working surface of said surgical fastener applying device into contact with said at least one article of pledget material.

5. The apparatus as set forth in claim 1 and further, said at least one article of pledget material having a peripheral edge which extends laterally past said at least one coupling aperture such that said at least one article of pledget material may be releasibly retained between said alignment means and said pressure equalization means.

6. The apparatus as set forth in claim 1 and further, wherein said pressure equalization means comprises a generally deformable and resilient material capable of releasibly biasing said at least one article of pledget material into contact with said alignment means when said at least one article of pledget material is disposed within said receiving area.

7. The apparatus as set forth in claim 1 and further, wherein said at least one guide channel is beveled having an engagement surface which angles laterally outward from said alignment means.

8. A surgical kit for facilitating application of an article of pledget material to the apposed working surfaces of a surgical fastener applying device for producing reinforced surgical fastener suture lines, comprising:
    an alignment means;
    at least one article of pledget material having a shape that generally complements the shape of said working surface of said surgical fastener applying device;
    pressure equalization means disposed in said alignment means for supporting and equalizing the pressure applied to said at least one article of pledget material during contact with said working surface of said surgical fastener applying device; and
    means for temporarily securing said at least one article of said pledget material to said working surface of said surgical fastener applying device.

9. The kit as set forth in claim 8 and further, said alignment means comprising a guide channel extending from a coupling aperture, and a receiving area open to said coupling aperture for housing said pressure equalization means.

10. The kit as set forth in claim 9 and further, wherein said guide channel is beveled having an engagement surface which angles laterally outward as said guide channel extends from said coupling aperture of said alignment means.

11. The kit as set forth in claim 8 and further, said at least one article of pledget material comprising host compatible tanned animal tissue.

12. The kit as set forth in claim 11 and further, wherein said host compatible tanned animal tissue is bovine pericardium.

13. The kit as set forth in claim 8 and further, said means for temporarily securing said at least one article of said pledget material to said working surface of said surgical fastener applying device comprising a cellulose-based adhesive.

14. An apparatus for providing reinforced surgical fastener suture lines, comprising:

retainer means having means for retaining at least one article of pledget material, means for guiding a working surface of a surgical fastener applying device into contact with said at least one article of pledget material, and means for uniformly applying said at least one article of pledget material onto said working surface of said surgical fastener applying device; and means for releasably attaching said at least one article of pledget material to said working surface of said surgical fastener applying device.

15. The apparatus as set forth in claim 14 and further, said means for retaining said at least one article of pledget material comprising a partially enclosed receiving area and a pressure equalization member disposed therewithin, said means for guiding a working surface of a surgical fastener applying device into contact with said at least one article of pledget material comprising at least one guide channel that is open to said receiving area.

16. The apparatus as set forth in claim 15 and further, said at least one guide channel having a beveled construction.

17. The apparatus as set forth in claim 16 and further, said means for releasably attaching said at least one article of pledget material to said working surface of said surgical fastener applying device comprising a cellulose-based adhesive.

18. The apparatus set forth in claim 15 and further, said pressure equalization member comprising a generally deformable and resilient material capable of releasably biasing said at least one article of pledget material into contact with said receiving area.

19. The apparatus as set forth in claim 15 and further, said retainer means including a alignment means and said pressure equalization member, wherein said receiving area extends within a sheath portion of said alignment means and said at least one guide channel extends from a coupling aperture formed within said sheath portion of said alignment means such that said at least one guide channel is open to said receiving area.

20. A method of retrofitting surgical fastener applying devices to produce reinforced surgical fastener suture lines, said surgical fastener applying device having a pair of apposed working surfaces, comprising the steps of:

(a) providing retaining means for releasably retaining an article of pledget material in physical contact with pressure equalization means;

(b) providing means for releasably attaching said article of pledget material to one of said pair of apposed working surfaces of said surgical fastener applying device; and (c) releasably attaching said article of pledget material on one of said pair of apposed working surfaces of said surgical fastener applying device.

21. The method as set forth in claim 20 and further, step (c) comprising the further sub-steps of:

(i) closing said pair of apposed working surfaces of said surgical fastener applying device about said retaining means to form a compressed state wherein said article of pledget material is compressed between said pressure equalization means and one of said pair of apposed working surfaces to engage said means for releasably attaching said article of pledget material to one of said pair of apposed working surfaces of said surgical fastener applying device; and (ii) moving said surgical fastener applying device away from said retaining means while in said compressed state so as to remove said pressure equalization means and said article of pledget material from said retaining means; and (iii) opening said pair of working surfaces of said surgical fastener applying device from said compressed condition so as to remove said pressure equalization means from said physical contact with said article of pledget material.

* * * * *